(12) United States Patent
Kiehne

(10) Patent No.: US 6,626,418 B2
(45) Date of Patent: Sep. 30, 2003

(54) NEEDLE FREE ACCESS VALVE

(75) Inventor: Bruce Leigh Kiehne, Slacks Creek (AU)

(73) Assignee: Occupational & Medical Innovations Pty. Ltd., Springwood (AU)

( * ) Notice: Subject to any disclaimer, the term of this patent is extended or adjusted under 35 U.S.C. 154(b) by 104 days.

(21) Appl. No.: 09/901,090

(22) Filed: Jul. 10, 2001

(65) Prior Publication Data

US 2002/0117645 A1 Aug. 29, 2002

(30) Foreign Application Priority Data

Feb. 23, 2001 (AU) .......................................... 23212/01

(51) Int. Cl.[7] .............................................. H01L 29/47
(52) U.S. Cl. ..................... 251/149.6; 251/212; 604/249
(58) Field of Search ........................... 251/149.6, 149.1, 251/212; 604/249, 246, 905

(56) References Cited

U.S. PATENT DOCUMENTS

| | | | | |
|---|---|---|---|---|
| 3,788,598 A | * | 1/1974 | German et al. | 251/149.6 |
| 4,007,909 A | * | 2/1977 | Buseth et al. | 251/149.6 |
| 5,269,771 A | * | 12/1993 | Thomas et al. | 251/149.1 |
| 5,353,837 A | * | 10/1994 | Faust | 604/249 |
| 5,360,413 A | | 11/1994 | Leason et al. | |
| 5,401,245 A | | 3/1995 | Haining | |
| 5,555,908 A | * | 9/1996 | Edwards et al. | 251/149.6 |
| 6,036,171 A | | 3/2000 | Weinheimer et al. | |
| 6,048,335 A | | 4/2000 | Mayer | |
| 6,063,062 A | * | 5/2000 | Paradis | 604/249 |
| 6,068,011 A | | 5/2000 | Paradis | |

FOREIGN PATENT DOCUMENTS

| | | |
|---|---|---|
| WO | WO 93/05839 | 4/1993 |
| WO | WO 97/00702 | 1/1997 |

\* cited by examiner

Primary Examiner—Gene Mancene
Assistant Examiner—John Bastianelli
(74) Attorney, Agent, or Firm—Hoffman, Wasson & Gitler, PC

(57) ABSTRACT

A one way valve assembly has an inlet and an outlet, the inlet forming one end of a tubular passageway, a valve member which is slideable along the tubular passageway between a closed position where fluid is unable to flow through the valve assembly, and an open position, the valve member having an outer end and an inner end, and biasing means to bias the valve member to the closed position, characterized in that when the valve member is in the closed position, the outer end is substantially at the inlet of the valve assembly to close of the tubular passageway and to allow the inlet area to be sterilized.

12 Claims, 9 Drawing Sheets

NEEDLE FREE ACCESS VALVE

FIELD OF THE INVENTION

This invention is directed to a needle free access valve for use in a needle free intravenous access system, and where the valve permits bi-directional flow when open. The valve finds particular use in the medical field.

BACKGROUND ART

A needle free access valve is one where the valve can be opened using a needleless syringe. A needleless syringe is a syringe where the needle has been removed such that the front of the syringe has only the luer taper or luer lock. Such valves are known but suffer from a number of disadvantages. A typical known valve has a body composed of two cylindrical containers. One container has a tubular opening into which the luer taper can be pressed. The other container has a tubular opening filled with a luer lock which allows the valve to be attached to various medical devices. Fluid flows through the luer taper upon depression of the syringe plunger and flows through the valve. The valve has a circular valve disk which can be forced open by the pressure of the fluid. When the fluid pressure stops, the valve returns to its closed position. This type of arrangement is entirely conventional. One disadvantage with this arrangement is that high levels of fluid flow can often not be obtained due to the design of the valve. That is, the valve itself is solid and fluid can flow only about the edge of the valve when the valve is opened. Another disadvantage is the lack of sterilisation around the inlet part of the valve. Sterilisation is critical as different devices can be inserted into the valve. For instance, a number of different syringes or fluid connections can be connected to the inlet part of the valve. It is essential to ensure that the valve does not become contaminated. With conventional valves, the luer taper of the syringe is pressed into the inlet part of the valve to hold the syringe to the valve. When the syringe is removed, the inlet part cannot be easily cleaned due to its small size and because it has a tubular configuration and it is difficult to clean and sterilise the inside part of the tubular configuration.

Other disadvantages with conventional valves is the production costs, the relatively large number of components making up the valve, the difficulty in mass production of the valve.

OBJECT OF THE INVENTION

The present invention is directed to a needle-free access valve which can be swabbed and sterilised between use, and which may at least partially overcome some of the above-mentioned disadvantages or provide the consumer with useful or commercial choice.

In one form the invention resides in a valve assembly which has an inlet and an outlet, the inlet forming one end of a tubular passageway, a valve member which is slideable along the tubular passageway between a closed position where fluid is unable to flow through the valve assembly, and an open position, the valve member having an outer end and an inner end, and biasing means to bias the valve member to the closed position, characterised in that when the valve member is in the closed position, the outer end is substantially at the inlet of the valve assembly to close off the tubular passageway and to allow the inlet area to be sterilised.

In this manner, when the valve member is in the closed position, the outer end is typically flush with the inlet to present a flush surface which can be swabbed or sterilised. With conventional valves, the tubular passageway remains completely open as the valve is usually at the bottom of the tubular passageway, and such an open passageway is a source of contamination which is difficult if not impossible to properly sterilise.

The valve assembly may be formed from two main parts being a top casing and a bottom casing which are fixed together in a permanent seal. The top casing typically has the inlet and the tubular passageway. The bottom casing typically has the outlet which may be configured or have some form of attachment means to allow the valve to be attached to other devices. The bottom casing is typically also substantially tubular. The top casing and the bottom casing may have a stepped configuration comprising a passageway of smaller diameter or cross-section adjacent the inlet and outlet, and a passageway of larger diameter or cross-section where the two parts meet. The passageway of larger diameter or cross-section can comprise an internal chamber.

The valve member may have different configurations depending on the operation of the valve assembly. In one form, the valve assembly is made from only nonmetallic parts and the biasing means does not comprise a helical spring. In this form of the invention, the valve member can have an "arrow shaped" configuration and may comprise a forward head part or plunger part, and a rear tail or stem part. The valve member may have at least one longitudinal passageway along which fluid can pass. The passageway may comprise an external passageway formed in the outside wall of the valve member and/or an internal passageway. Preferably, the valve member is provided with at least one longitudinal external passageway formed in the stem part of the valve member which communicates with at least one internal passageway extending through the plunger part of the valve member. In this manner, fluid can pass along and through the valve member and therefore through the valve assembly. In this form of the invention, the stem part of the valve member can be positioned in the tubular passageway which comprises the inlet, and the plunger part of the valve member can be positioned in the chamber. The valve member has an outer end and an inner end. In this form of the invention, the outer end may comprise an end wall of the stem, and the inner end may comprise a forward portion of the plunger part. A sealing means may be provided to seal the valve member against fluid flow when the valve member is in the closed position. The outer end may comprise or be associated with sealing means to seal this part of the valve member against the tubular passageway and against passage of fluid. Alternatively, or in addition thereto, the plunger part may have a sealing face which seals against part of the tubular passageway and/or an internal wall of the chamber.

A biasing means is provided to bias the valve member to the closed position. In this form of the invention, the biasing means may comprise a torsion ring which can be fitted into the chamber. The torsion ring may be provided with a plurality of finger members having one end attached to or forming part of the ring, and having the free end tapering to the free end of the other finger members. The torsion ring and the finger members are preferably configured to complement the shape of the plunger part of the valve member and function to bias the valve member to the closed position.

In a second embodiment, the valve assembly has a helical spring which comprise the biasing means, and the valve member is formed from two parts which can comprise a stationary part, and a moving part. In this second embodiment, the valve assembly may comprise a housing having an inlet and an outlet with the inlet forming one end of a tubular passageway. The valve member may comprise an inner stationary part and an outer moving part which can reciprocate along the inner stationary part. The outer moving part can be moved between a closed position where fluid is unable to flow through the valve assembly, and an open position. The outer moving part, when in the closed position, is substantially at the inlet of the valve assembly. The outer moving part may comprise a sliding cap. The inner stationary part may comprise an elongate peg or rod. The inner part typically has an outer end which is substantially at the inlet of the valve assembly, and an inner end which can be secured to the inside of the housing to fix the inner part in place. The outer part typically has a peripheral inside wall which is formed with a sealing surface to seal against a portion of the inner wall of the tubular passageway when the valve member is in the closed position. Preferably, the closed position is where the outer part is substantially at the inlet of the valve assembly and presents a substantially flush surface with the inlet. The outer part may be provided with a passageway or bore which can allow the outer part to be mounted to the inner part. The passageway is typically circular. When the valve member is in the closed position (typically when the outer part is adjacent the inlet) it is preferred that the inner part has a configuration which provides a sealing engagement with the passageway or bore in the outer part to prevent any fluid from passing through the valve assembly. The outer part can be pushed along the inner part to an open position where it is preferred that the configuration of the inner part is such that fluid can flow through the bore and through the valve assembly.

Suitably, the tubular passageway is formed with recesses at a position spaced away from the inlet such that when the outer member is in this part of the tubular passageway, fluid can pass between the outer member and the tubular passageway. The biasing means may comprise a helical spring extending about the inner part and functioning to bias the outer part towards the inlet.

In a third embodiment, the valve assembly comprises a single valve member which may comprise a head part and a stem part and the biasing means may comprise a helical spring about the stem part. In this embodiment, the head part may slide along the tubular passageway between a closed position where the head part is substantially at the inlet, and an open position where the head part is pushed downwardly along the tubular passageway. The tubular passageway may be provided with at least one recess spaced away from the inlet to facilitate fluid flow past the head part.

BRIEF DESCRIPTION OF THE DRAWINGS

Embodiments of the invention will be described with reference to the following figures.

BEST MODE

Figure 1:
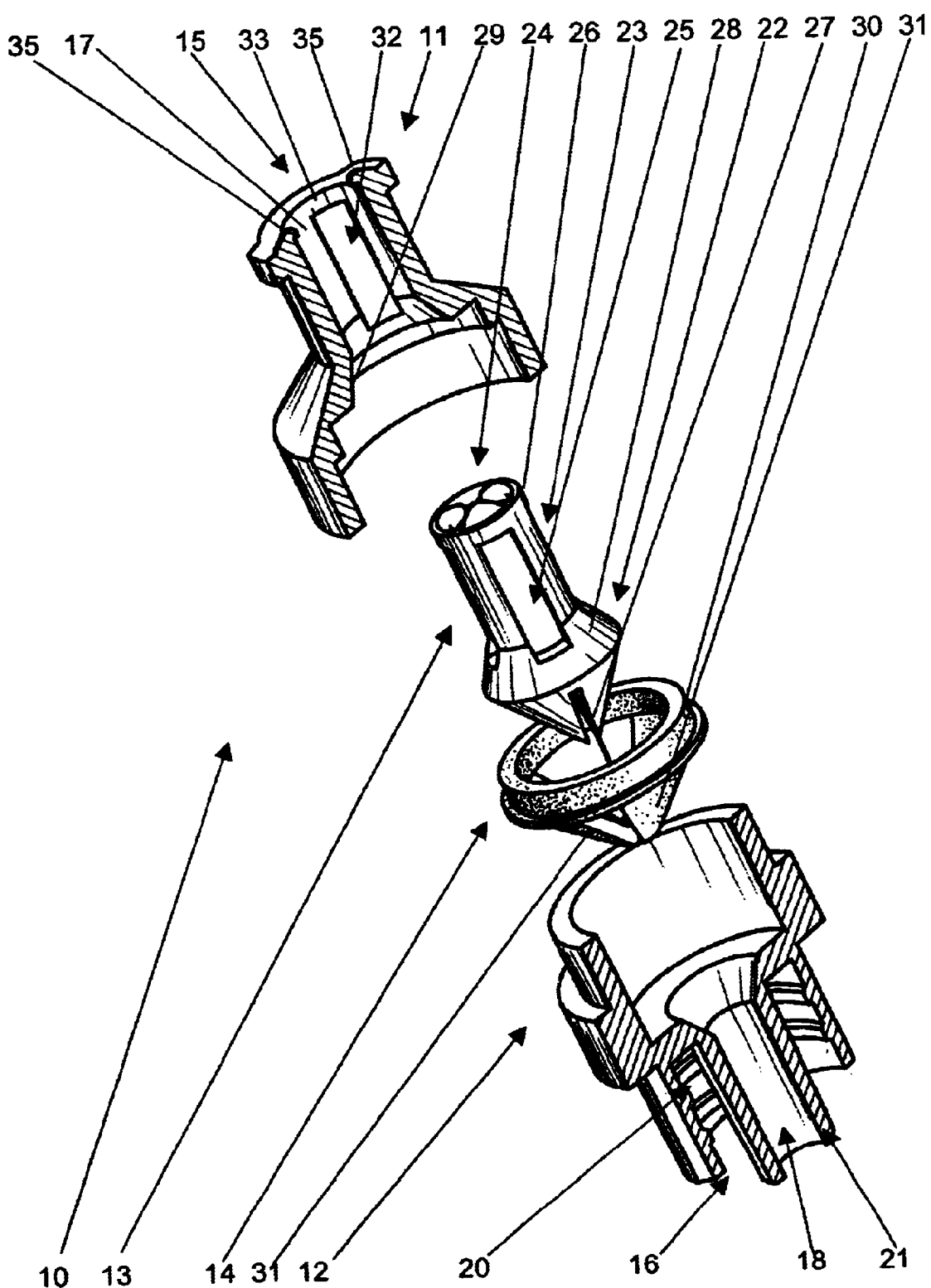
FIG. 1 is an exploded view in part section of a valve assembly according to a first embodiment of the invention.
Figure 2:
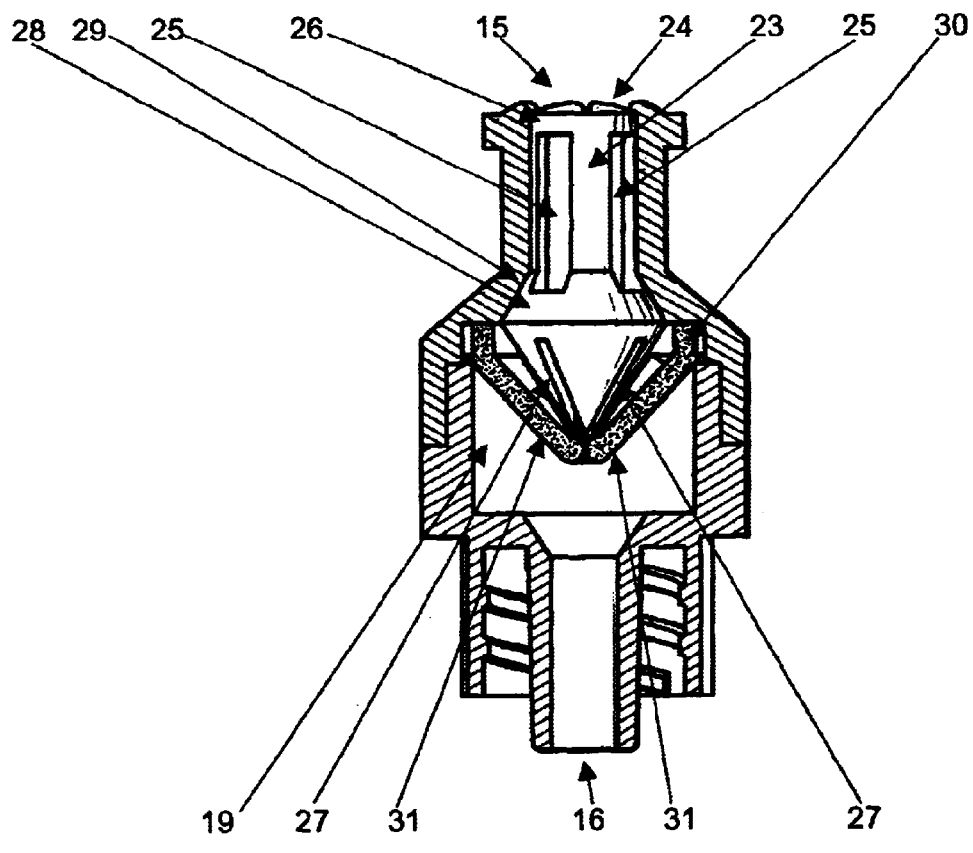
FIG. 2 is an assembled section view of the valve assembly according to the first embodiment of the invention in the closed position.

Referring initially to the first embodiment of the invention illustrated in FIGS. 1–4, there is disclosed a valve assembly 10. The valve assembly is made from four separate components which comprise an external housing which consists of a top casing 11 and a bottom casing 12, an internal valve member 13 and an internal biasing means 14. The housing can be made from polycarbonates or similar material. The top casing and the bottom casing are bonded together in a permanent seal. Each casing is substantially hollow to define an internal substantially circular passageway. Each casing has a stepped internal passageway. Top casing 11 has an inlet 15 while bottom casing 12 has an outlet 16. In top casing 11, inlet 15 communicates or forms part of a first tubular passageway 17 of smaller diameter, which opens up into a second tubular passageway of larger diameter. Similarly, bottom casing 12 has an outlet 16 which communicates or forms part of a first tubular passageway 18 of smaller diameter which opens up into a second tubular passageway of larger diameter. When the two casings are joined together, the second tubular passageways forms a chamber 19. Outlet 16 may be provided with threads 20 and a spigot 21 to enable the valve assembly to be coupled to other devices. This arrangement is a conventional luer lock.

Valve member 13 is "arrow" shaped and comprises a forward plunger part 22 and a rear stem part 23. Rear stem part 23 is cylindrical and has an outer end 24. The stem part 23 slides along passageway 17. The stem part 23 is provided with a plurality of longitudinal passageways or slots 25. These passageways comprise recesses in the outside wall of the stem part which means that the main body of the stem part is solid. The recesses terminate at a position spaced away from outer end 24 to provide a sealing band 26. This sealing band 26 is in sealing but sliding engagement against the inside wall of passageway 17 when the valve member is in the closed position illustrated in FIG. 2. Thus, in this position, the sealing band 26 forms a first seal against passage of fluid through the valve member. As well, in this position, outer end 24 is substantially flush with inlet 15 which means that the inlet can be sterilised or swabbed, and the tubular passageway 17 is not exposed to germs and bacteria when the valve is in the closed position.

The plunger part 22 has the shape of a tapered cone and the foremost part of the cone comprises the inner end of the valve member. The plunger part is provided with slots 27 which pass through the body of the plunger part and which communicate with the lower end of passageways 25. Thus, fluid can flow along passageway 25 and through a respective slot 27 to allow fluid to flow through the valve assembly. The junction between the plunger part 22 and the stem part 23 provides a second sealing surface 28 for the valve member. The second sealing surface 28 seals against a complimentary configured part 29 of top casing 11 when the valve is in the closed position illustrated in FIG. 2.

The valve assembly contains a biasing means 14. The biasing means 14 is in the form of a torsion ring 30 and a plurality of sprung fingers 31. The torsion ring 30 and the sprung fingers 31 are formed as a unitary body and are fitted in the chamber 19 of the valve assembly. The fingers 31 adopt a natural position as illustrated in FIG. 1 where the fingers taper towards each other. If the fingers are pushed apart, the fingers will be biased to naturally push back towards the position illustrated in FIG. 1. The fingers 31 and the torsion ring 30 together bias the valve member to the closed position illustrated in FIG. 2.

Figure 3:
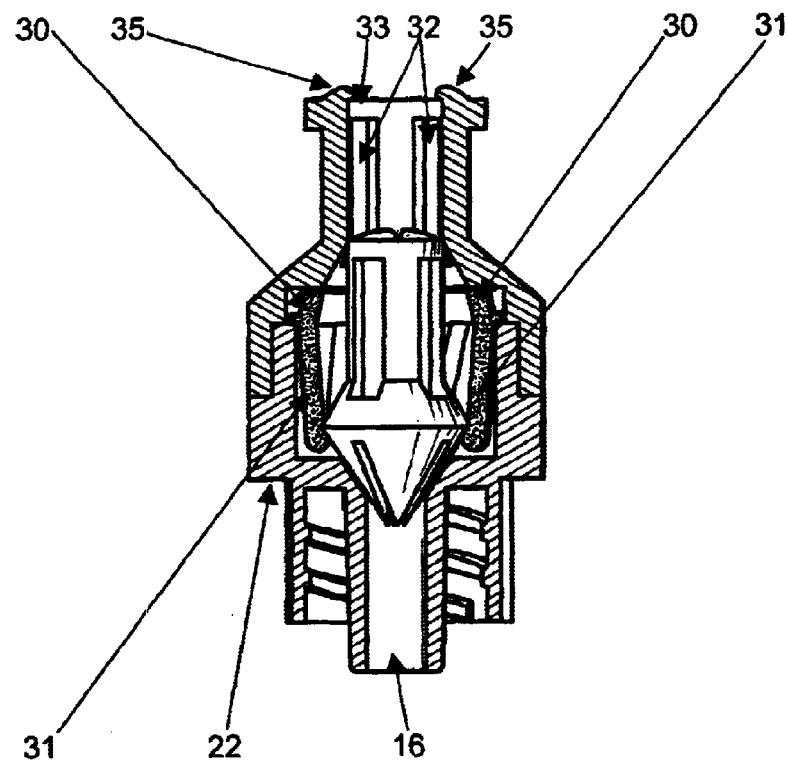
FIG. 3 is the valve assembly of FIG. 2 in the open position.
Figure 4:
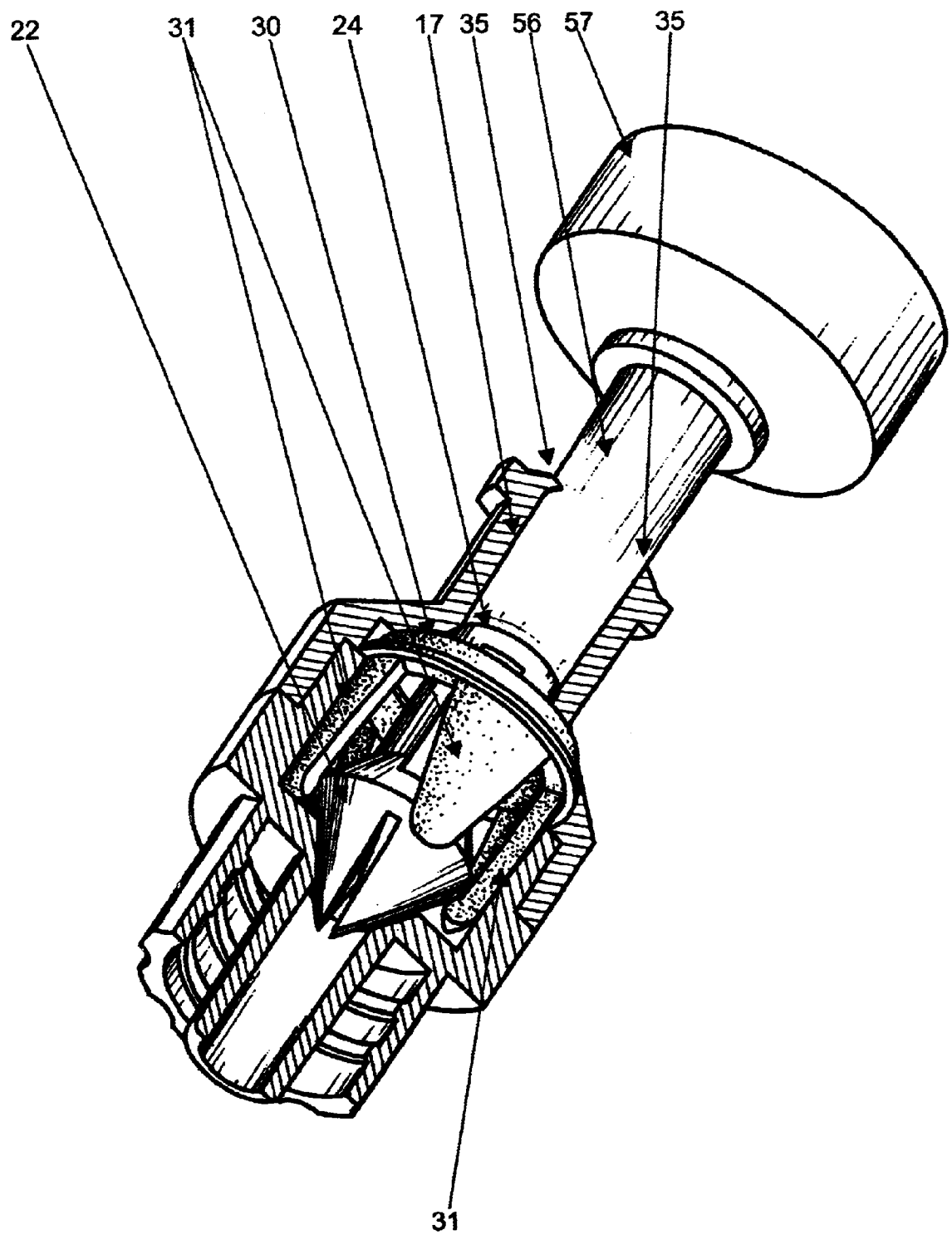
FIG. 4 is a part section view of the first embodiment showing the luer tip of a syringe pushing the valve member into the open position.

In use, the luer tip 56 of a syringe 57 (see FIG. 4) is pushed against outer end 24 of the valve member. This action will cause the valve member to be depressed along passageway 17 to the open position illustrated in FIG. 3. The luer tip 56 will also be pushed into passageway 17. As the valve member is depressed into the passageway to the position illustrated in FIG. 3, the plunger part 22 pushes against and opens up the sprung fingers 31. As well, the torsion ring 30 is twisted open which is best illustrated in FIGS. 3–4. The internal wall of passageway 17 is provided with longitudinal recesses 32 (see FIGS. 1 and 3). These recesses terminate at a position spaced inwardly from inlet 15 to provide a sealing band 33 which seals with the sealing band 26 on the valve member. Thus, when the valve member is in the closed position, the valve member seals against the internal wall of passageway 17. However, when the valve member is depressed, sealing band 26 on the valve member moves past the internal passageways 32 which now allows fluid to flow between the valve member and the wall of passageway 17. The passageways 25 on the external wall of the stem portion of the valve member also assist in passage of fluid. Fluid can now flow from the syringe along passageways 32, along passageways 25 and through slots 27 towards outlet 16. When the syringe is removed from passageway 17, the open sprung fingers 31 together with the twisted torsion ring 30 will function to push or bias the valve member back to the position illustrated in FIG. 2. In this position, inlet 15 is sealed and presents a flush face for sterilisation.

The luer tip 56 can be held in passageway 17 by providing small barbed projections 35 adjacent inlet 15. These projections bite into the luer taper at the full depth of travel. Projections 35 can be disengaged with an anticlockwise twist on the syringe. In this first embodiment, the fluid flow has minimal restriction because of the open passageway between and around the valve member and the biasing means. The valve member is able to remain depressed for long periods of time due to the memory characteristics of the torsion spring material.

Figure 5:
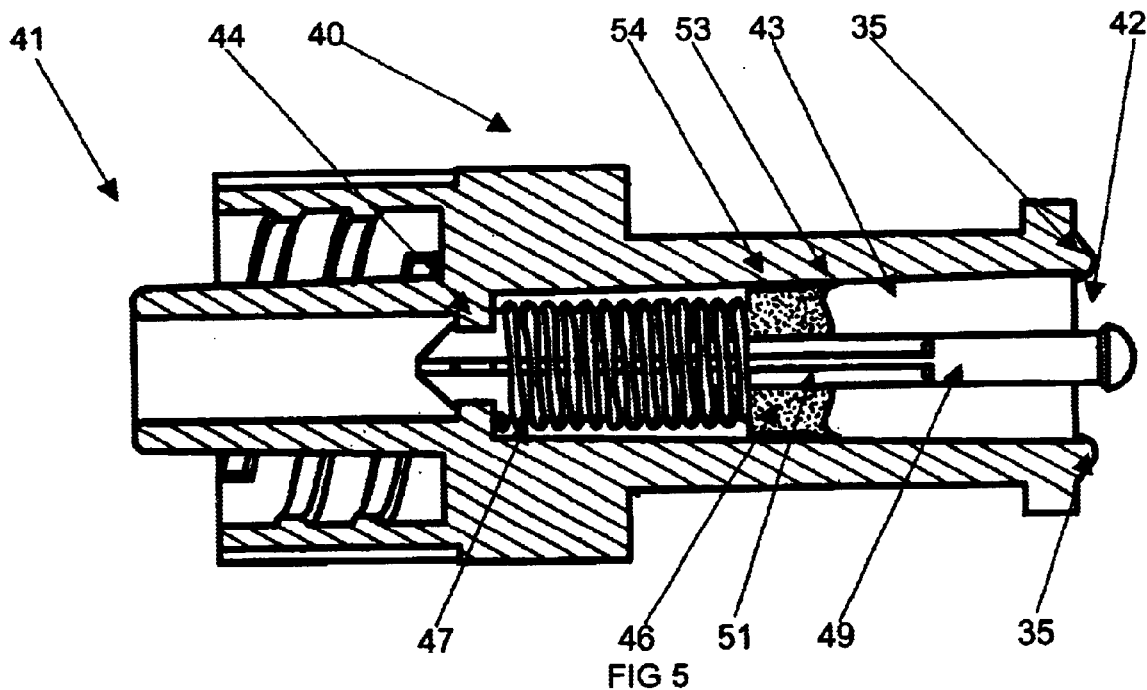
FIG. 5 is a section view of a valve assembly according to a second embodiment which is in the open position.
Figure 6:
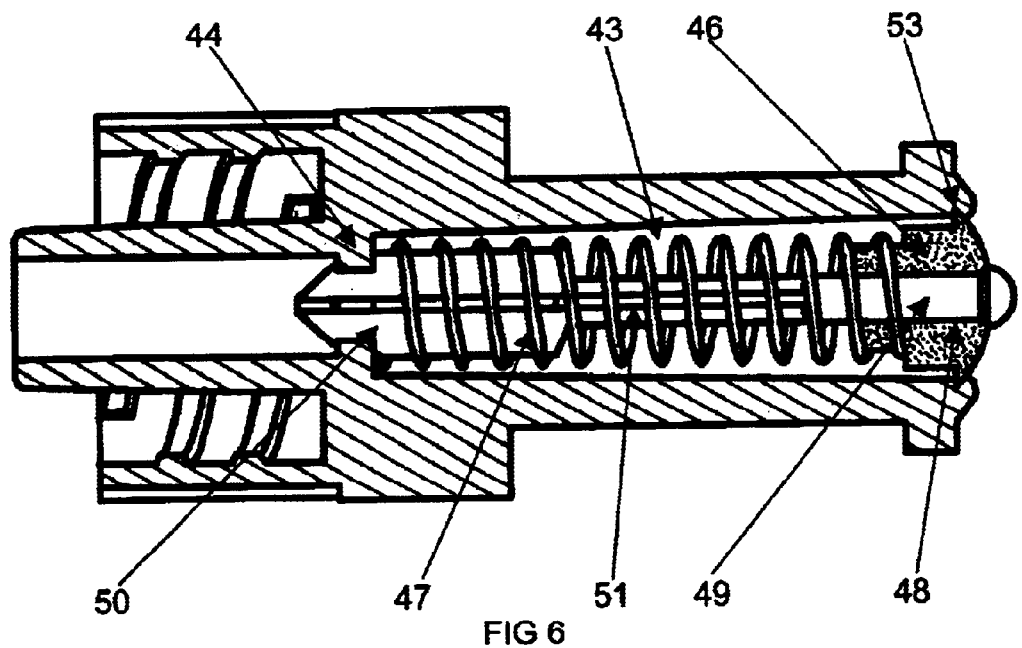
FIG. 6 is a section view of the valve assembly of FIG. 5 in the closed position.
Figure 7:
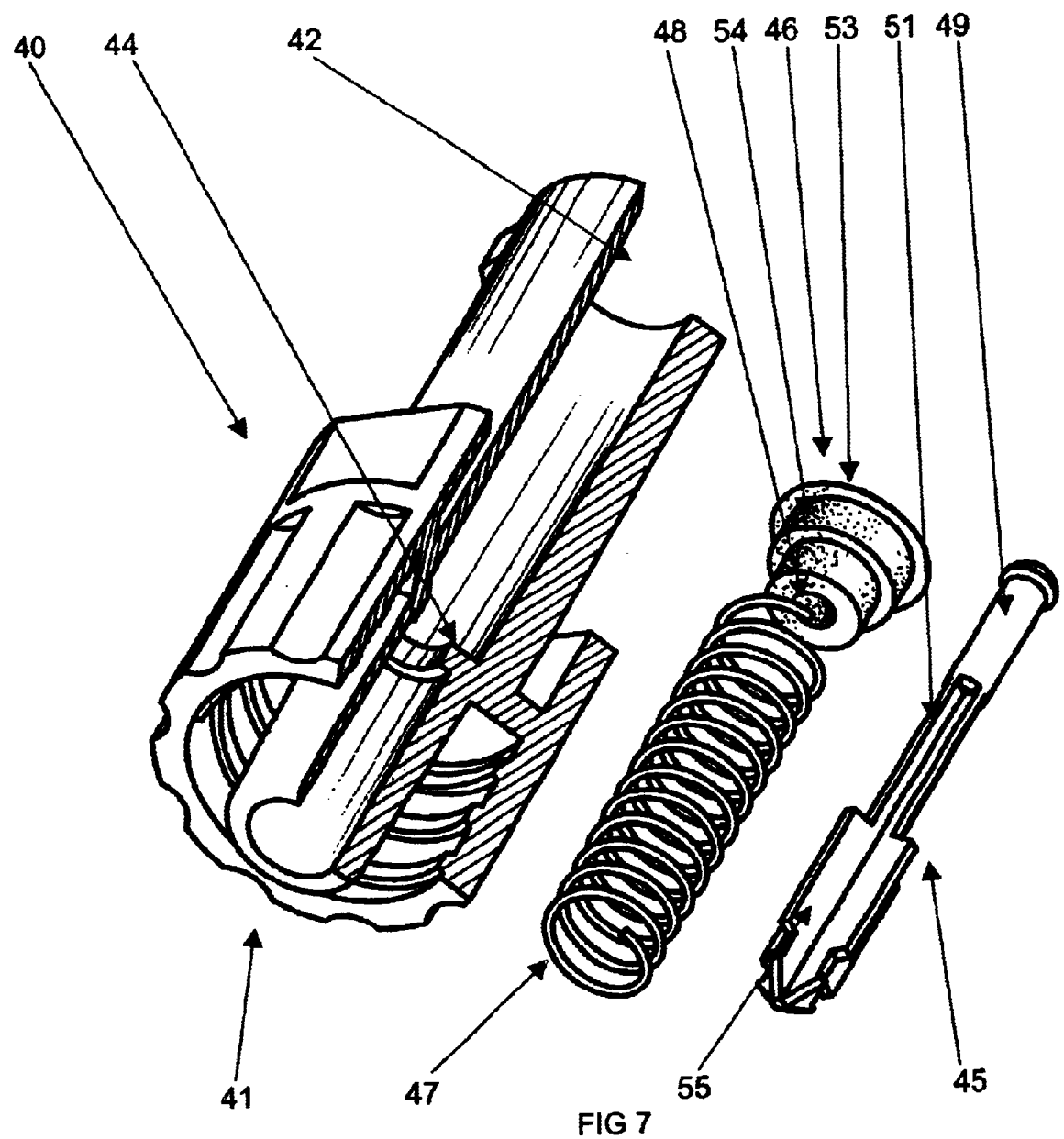
FIG. 7 shows the various components of the valve assembly according to the second embodiment of the invention.

A second embodiment of the invention is illustrated in FIGS. 5–8. In this embodiment, the valve assembly comprises a one-piece moulded housing 40 which has a standard luer lock 41 which forms part of the outlet. Housing 40 has a top inlet 42 which is provided with a pair of small barbed projections 35 similar to that described above. Inlet 42 forms part of an internal longitudinal passageway 43 which is best illustrated in FIGS. 5–6. Passageway 43 is circular and has an internal ring shaped stepped portion 44 the reason for which will be described below. In the second embodiment, the valve member is formed from two parts being an inner stationary part or peg 45 (see FIG. 7), and an outer part or cap 46 (see FIG. 7). Cap 46 is biased by a steel helical spring 47 (see FIG. 7) into a naturally closed position where cap 46 is substantially flush with inlet 42, this being best illustrated in FIG. 6. Cap 46 has an internal circular longitudinal passageway 48. Peg 45 has an outer end 49 and an inner end 50. Outer end 49 is solid and cylindrical and passes through passageway 48 in a sliding and sealing manner. This means that when cap 46 is in the closed position flush with inlet 42, the cap is also around the solid and cylindrical outer end 49 of peg 45 which prevents fluid from passing through the passageway 48.

Figure 8:
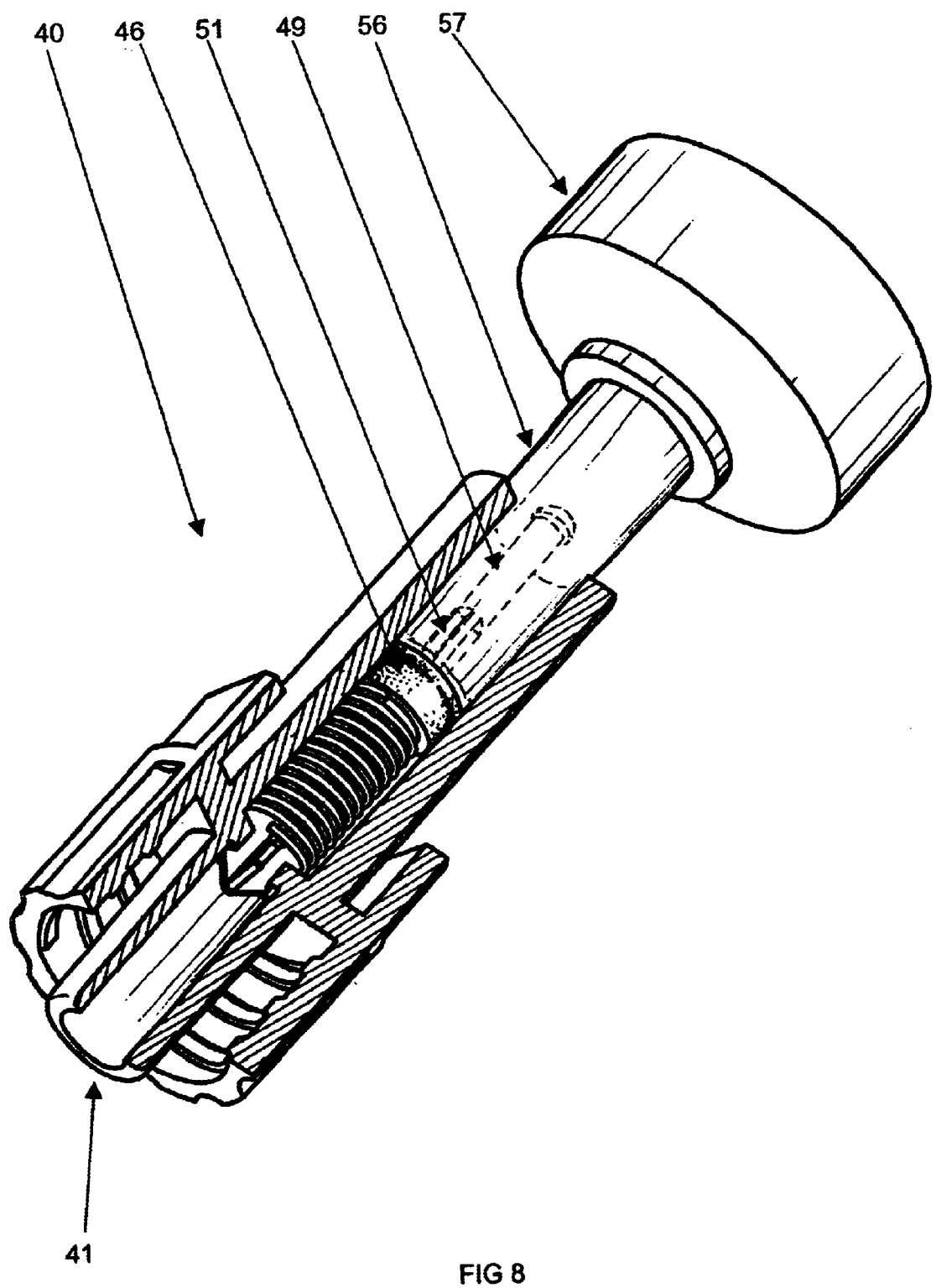
FIG. 8 illustrates in part section the valve assembly according to the second embodiment of the invention where the valve member is pushed into the open position by the luer tip of a syringe.

Peg 45 has a section 51 which is not cylindrical but which instead has a X-type configuration. When cap 46 slides along peg 45 and is in this section 51, fluid can now pass through passageway 48 as the X configuration part of the peg is now in the passageway. Peg 45 is fixed inside passageway 43 by locking the inner end 50 of peg 45 against the ring shaped stepped portion 44. This is best illustrated in FIG. 8. Thus, peg 45 does not move during use of the valve assembly.

In use, the valve assembly of the second embodiment is initially in the closed position illustrated in FIG. 6. In this position, cap 46 which is a semi-flexible sliding seal cap seals the top face or inlet 42 of the valve assembly thereby presenting a swabbable surface. Cap 42 has a peripheral lip 53 which can be deformed, and when the cap is in the closed position illustrated in FIG. 6, peripheral lip 53 overlies the edge of inlet 42. The luer tip 56 of a syringe 57 is pushed against the outer face of cap 46 (FIG. 8) which causes cap 46 to be pushed into passageway 43 and along peg 45. Initially, the peripheral lip 53 is deformed as the cap is pushed into passageway 43. The luer tip is also inserted into the passageway and can be held in place by the locking barbs 35 in a manner described above. The side wall 54 and/or the deformed lip 53 of cap 46 provides a seal to prevent fluid from passing through the valve assembly. As cap 46 is slid down peg 45, it will slide over the X shaped portion 51 at which time fluid can now pass through passageway 48 and through the valve assembly. At the point of full depression, cap 46 will abut against stop 55 (see FIG. 7) on peg 45 but fluid will still be able to flow will through passageway 48. The outer end 49 of peg 45 passes into the luer tip 56 of syringe 57 (see FIG. 8), but as this end has a relatively small diameter, it does not substantially impede fluid flow. If desired, longitudinal fluid flow passageways (not illustrated) can be provided in the wall of passageway 43 in a manner similar to that described above to facilitate passage of fluid through the valve assembly. Upon removal of the syringe, spring 47 functions to push cap 46 back to the closed position where the cap is substantially flush with the inlet.

Figure 9:
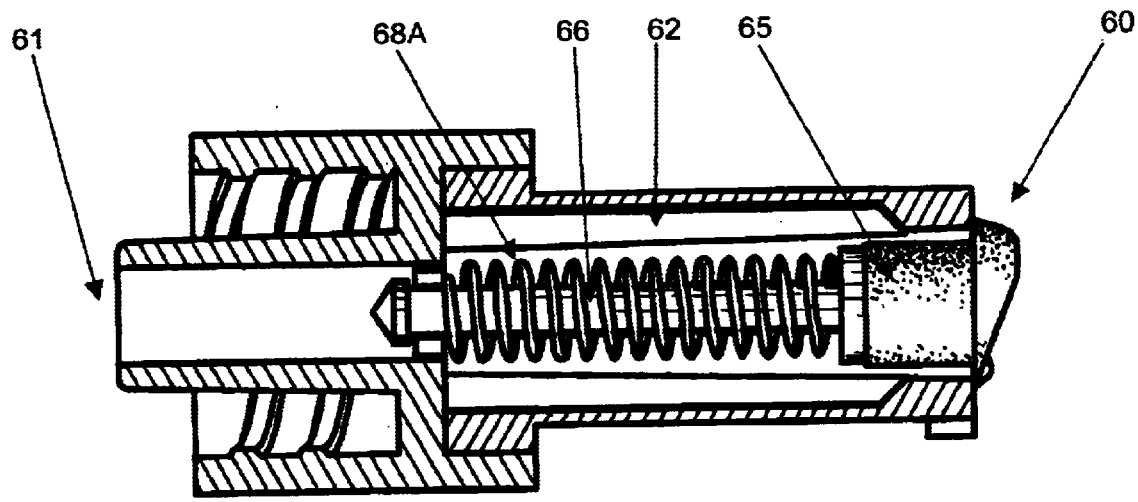
FIG. 9 illustrates in part section a valve assembly according to a third embodiment of the invention in the closed position
Figure 10:
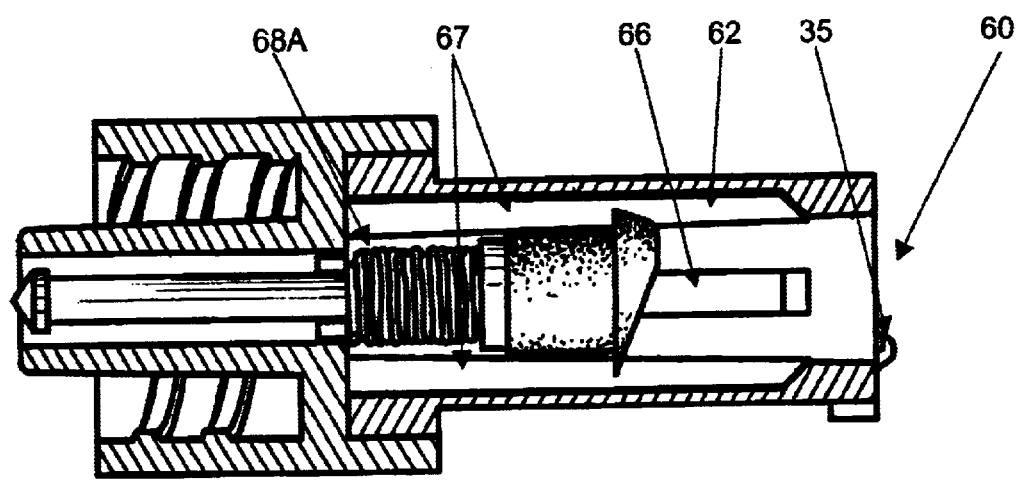
FIG. 10 illustrates in part section the valve assembly of FIG. 9 in the open position.
Figure 11:
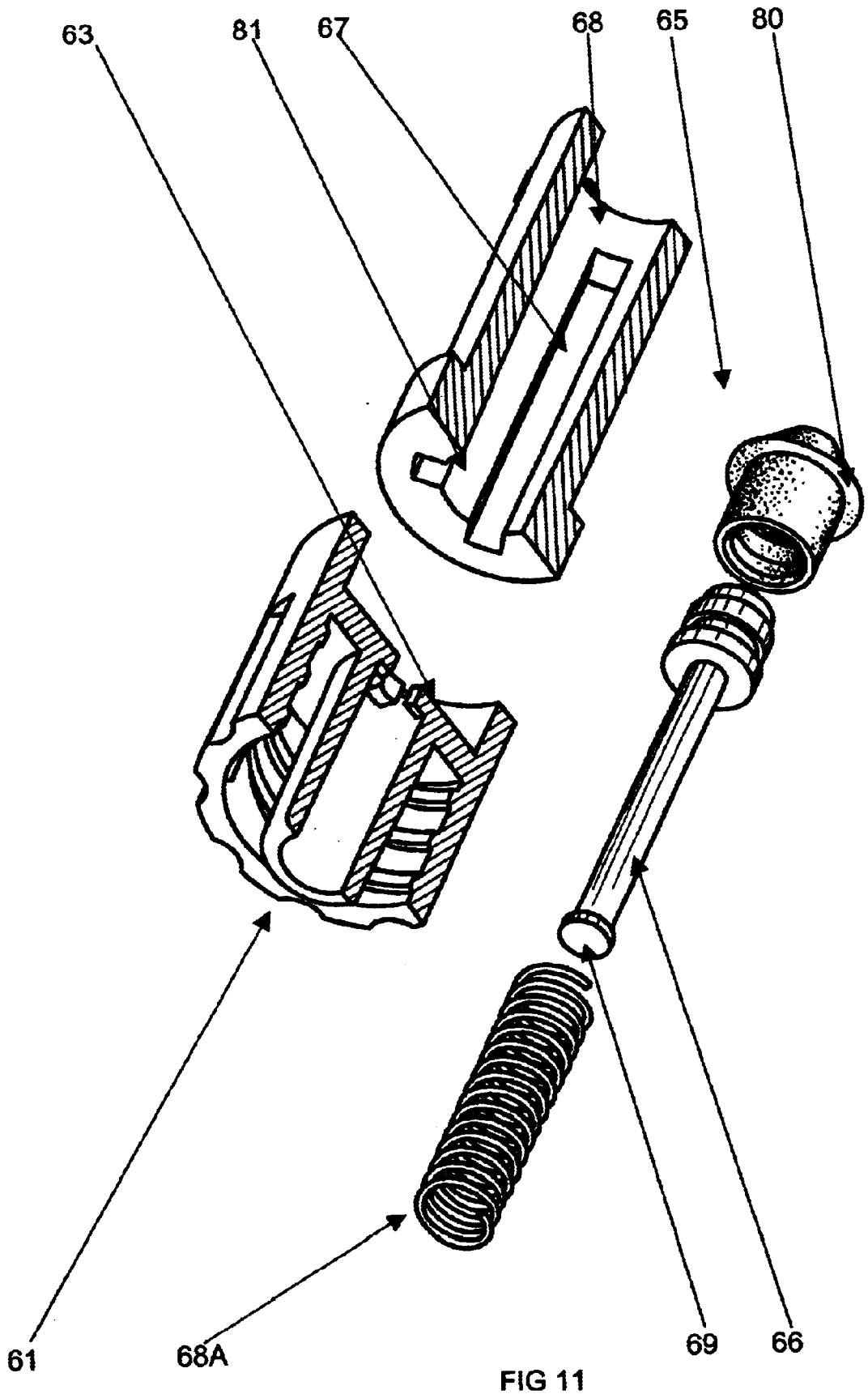
FIG. 11 illustrates the various components of the valve assembly according to the third embodiment of the invention.
Figure 12:
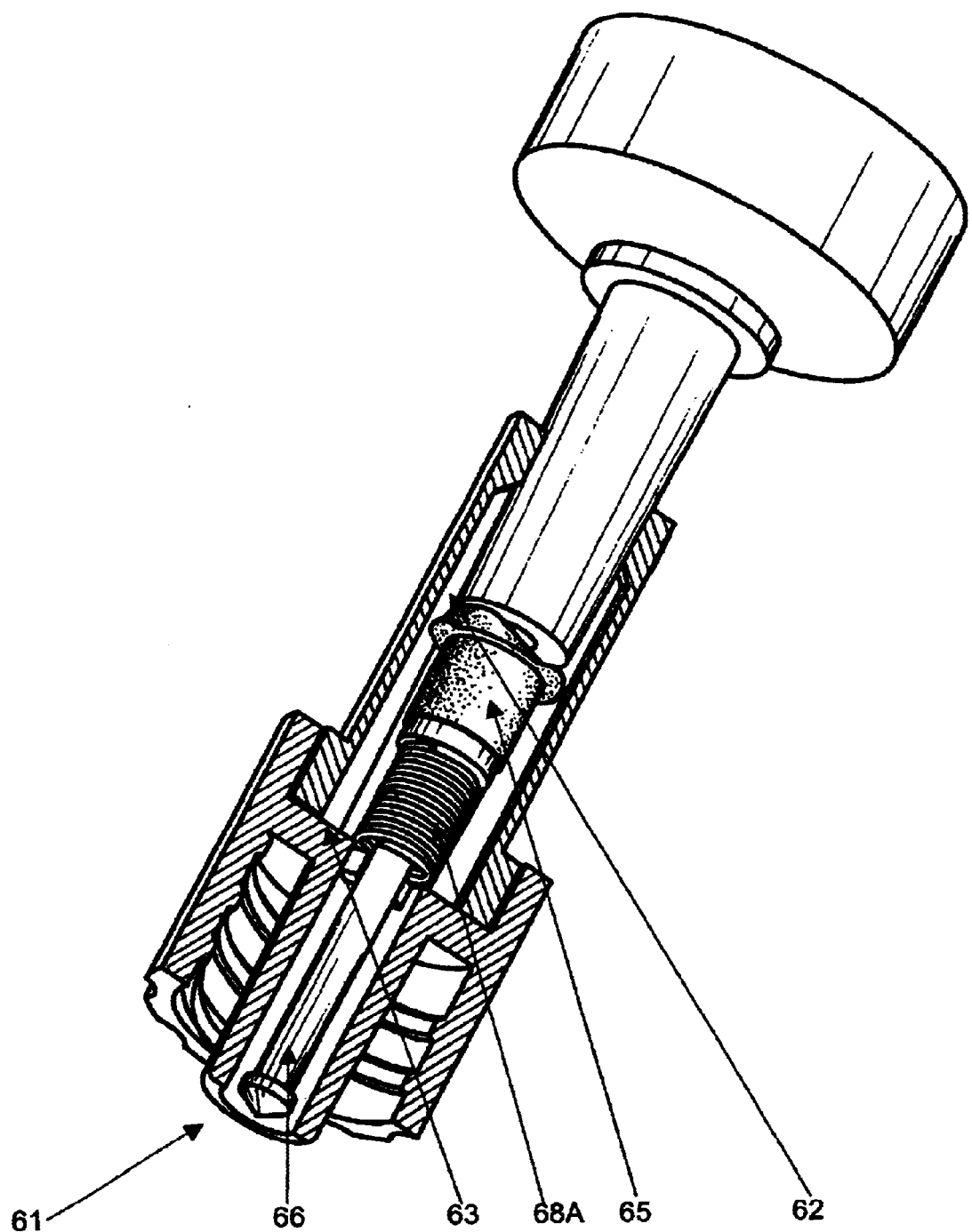
FIG. 12 illustrates in part section the valve assembly according to the third embodiment of the invention where the valve member is pushed in the open position by a luer tip of a syringe.

A third embodiment of the invention is described with reference to FIGS. 9–12. In this embodiment, the valve assembly has an outer housing which is similar to that described with respect to the second embodiment and which has an inlet 60 and an outlet 61 the outlet having the standard luer lock arrangement. An internal passageway 62 is provided which is best illustrated in FIGS. 9 and 10. The internal passageway has a restriction or step 63 which functions to hold the valve member as will be described in greater detail below. The valve member 64 has a head or cap 65 and an elongate rod or peg 66 which is attached to cap 65 in a fixed manner. That is, cap 65 does not slide along peg 66 in the manner described with reference to the second embodiment. Instead, depression of cap 65 by the syringe will cause cap 65 to be pushed into passageway 62 and attached peg 66 will be depressed into the outlet area 61. Cap 65 again has a peripheral lip 80 which can be deformed and which overlies the edge of inlet 60 when the cap is in the closed position illustrated in FIG. 9. In this position, the cap seals the passageway against contamination and also against passage of fluid. When the cap is pushed into the passageway, the internal walls of the passageway are provided with longitudinal recesses 67 (see FIG. 11) which allows fluid to pass between the cap and the wall of the recess when the cap is depressed. The recesses 67 terminate short of inlet 60 to again provide a sealing area 68 (see FIG. 11) to seal against the cap when the cap is in the closed position. A helical spring 68A extends about peg 66. Spring 68A extends underneath cap 65 and sits on top of step 63 which locks the peg to the remainder of the valve assembly. The top of cap 65 is sloped to provide a fluid flow gap when the luer tip presses against this portion.

I claim:

1. A one way valve assembly which has;

an outer valve body which contains an inlet and an outlet and which has a tubular passageway, the inlet forming one end of the tubular passageway, a valve member which is slideable along the tubular passageway between a closed position where fluid is unable to flow through the valve assembly, and an open position where fluid can flow through the valve assembly, the valve member having a plunger part and a stem part, the stem part having at least one longitudinal recess on an outer wall of the stem part, the plunger part having at least one slot extending there through, the slot being in communication with the recess, the recess and slot functioning to allow fluid to pass through the valve assembly upon movement of the valve member to the open position biasing means to bias the valve member to the closed position, the biasing means comprising a plurality of finger members which are pushed apart by the plunger part of the valve member when the valve member moves to the open position, and which finger members are biased to push the valve member back to the closed position.

2. The assembly of claim 1, wherein the valve member has an outer end and an inner end, the outer end, when the valve member is in the closed position, being substantially at the inlet of the valve assembly to close off the tubular passageway and to allow the inlet area to be sterilised.

3. The assembly of claim 2, wherein the valve body is formed from two main parts being a top casing and a bottom casing which are fixed together in a permanent seal.

4. The assembly of claim 3, wherein the top casing has the inlet and the tubular passageway and the bottom casing has the outlet which is configured or has an attachment means to allow the valve to be attached to other devices.

5. The assembly of claim 1, wherein the valve body has an internal area which comprises a passageway of smaller cross-section adjacent the inlet and outlet, and a chamber which comprises a passageway of larger cross-section intermediate the inlet and the outlet.

6. The assembly of claim 5, wherein the stem part of the valve member is positioned in the tubular passageway which comprises the inlet, and the plunger part of the valve member is positioned in the chamber.

7. The assembly of claim 2, wherein the outer end of the valve member comprises an end wall of the stem part, and the inner end comprises a forward portion of the plunger part.

8. The assembly of claim 1 comprising a sealing means provided to seal the valve member against fluid flow when the valve member is in the closed position.

9. The assembly of claim 8, wherein the plunger part has a sealing face which seals against part of the tubular passageway and/or an internal wall of the chamber.

10. The assembly of claim 5, wherein the biasing means comprises a torsion ring which is fitted into the chamber.

11. The assembly of claim 10, wherein the torsion ring is provided with said plurality of finger members, each finger member having one end attached to or forming part of the ring and having another free end tapering to the free end of the other finger members.

12. The assembly of claim 11, wherein the torsion ring and the finger members are configured to complement the shape of the plunger part of the valve member and function to bias the valve member to the closed position.

* * * * *